United States Patent [19]
Tang et al.

[11] Patent Number: 5,481,584
[45] Date of Patent: Jan. 2, 1996

[54] DEVICE FOR MATERIAL SEPARATION USING NONDESTRUCTIVE INSPECTION IMAGING

[76] Inventors: Jihong Tang, 14 Bayporte, Irvine, Calif. 92714; Yao-Jin Qian, 16401 Santa Anita La., Huntington Beach, Calif. 92649

[21] Appl. No.: 344,171

[22] Filed: Nov. 23, 1994

[51] Int. Cl.$^6$ ................................................. G01N 23/06
[52] U.S. Cl. ................................................. 378/98.9; 378/53
[58] Field of Search ........................... 378/98.8, 98, 98.2, 378/45, 46, 49, 53, 57, 83, 82, 88

[56] References Cited

U.S. PATENT DOCUMENTS

| | | | |
|---|---|---|---|
| 4,029,828 | 6/1977 | Bildstein et al. | 427/34 |
| 4,132,916 | 1/1979 | Hueschen et al. | 313/330 |
| 4,587,555 | 5/1986 | Carollo et al. | 250/353 |
| 4,686,695 | 8/1987 | Macovski | 378/146 |
| 4,731,805 | 3/1988 | Boyarina et al. | 378/125 |
| 4,759,047 | 7/1988 | Donges et al. | 378/58 |
| 4,791,655 | 12/1988 | Nagata et al. | 378/57 |
| 4,799,247 | 1/1989 | Annis et al. | 378/57 |
| 4,916,722 | 4/1990 | Ema | 378/98.2 |
| 4,918,713 | 4/1990 | Honda | 378/87 |
| 4,926,454 | 5/1990 | Haendle et al. | 378/100 |
| 4,945,552 | 7/1990 | Ueda et al. | 378/156 |
| 5,018,179 | 5/1991 | Kaneko | 378/98.12 |
| 5,042,055 | 8/1991 | Wirt et al. | 378/59 |
| 5,163,077 | 11/1992 | Dupre et al. | 378/51 |
| 5,233,639 | 8/1993 | Marks | 378/42 |
| 5,296,937 | 3/1994 | Nakatani et al. | 378/98.12 |
| 5,319,547 | 6/1994 | Krug et al. | 364/409 |

*Primary Examiner*—David P. Porta
*Assistant Examiner*—Don Wong
*Attorney, Agent, or Firm*—Price, Gess & Ubell

[57] ABSTRACT

Device and method are provided for separating images according to material species in nondestructive x-ray or γ-ray imaging. Using the x-ray (or γ-ray) attenuation coefficient of materials as functions of x-ray energy, simultaneous linear equations are set up and solved for obtaining the image for a specific material when multiple x-ray (or γ-ray) energies are used. The device disclosed in this invention features real-time, material-specific image separation. Applications include x-ray security inspection and industrial x-ray or γ-ray noninvasive structural inspection.

43 Claims, 9 Drawing Sheets

DEVICE FOR MATERIAL SEPARATION USING NONDESTRUCTIVE INSPECTION IMAGING

BACKGROUND OF THE INVENTION

1. Field of the Invention

This invention relates to the general field of nondestructive radiation inspection using x-ray or γ-ray imaging systems,

2. Description of Related Art

A single x-ray (or γ-ray) energy band with finite band width has been used in conventional nondestructive projection imaging. Such imaging systems use the accumulated attenuation information of all the materials within the region of imaging interest and cannot distinguish one material from another when two different materials contribute to the same amount of attenuation. For example, a thin metal plate and thick plastic plate may not be distinguishable with single energy projection imaging.

An improvement from single energy projection imaging is the use of two different x-ray energy bands (a high energy band and a low energy band) and the ratio of material attenuation coefficients at these different energies, $\mu_H/\mu_L$ (U.S. Pat. No. 4,982,584). When the ratio is close to one, the object is identified as plastic; when the ratio is less than one, the object is identified as metal. Such a method can discern plastic from metal only if the region of interest does not contain overlapping of both materials. Also, when the high energy band is above and near an absorption edge of the metal (e.g. a K edge), the ratio of the material attenuation coefficients may be close to one (indicating plastic), even though the region of interest contains metal. The distinction between plastics and metals is thus made difficult when the high energy band used is close to a K edge of a metal in the region of interest.

A further improvement along the attenuation coefficient ratio method can be found in U.S. Pat. No. 5,319,547. This technique depends on the comparison of x-ray transmission between a reference region and its neighbor at different x-ray energies. This method cannot solve for the thickness information of materials or distinguish among more than two different materials existing in the same region of interest.

In the medical field of angiography, two appropriately filtered different x-ray energies have been used to identify iodine contrast in a region of interest containing iodine, bone, and tissue. This image subtraction technique incorporates the difference of linear absorption coefficients at different x-ray energies. Two different x-ray energies at which the bone and tissue attenuation coefficients are very close to each other are used to produce two different x-ray images. A weighted subtraction of the images is performed to eliminate the bone and tissue images and to sort out the iodine image. When residual bone background images remain after subtraction, a third energy below the iodine absorption K edge may be added to cancel the residual bone background and to isolate the iodine-filled blood vessel image (U.S. Pat. No. 4,686,695, 1987). This technique is specified with materials existing in the human body that are known prior to imaging such as bone, tissue, iodine contrast, and lesion. According to this particular technique, the two x-ray energies should be chosen such that the bone and tissue mass attenuation coefficients are close to each other at the two x-ray energies. Another limitation is that when the third energy is needed for eliminating residual bone images, it should be chosen to be below the iodine or lesion absorption edge. Moreover, this technique does not operate and produce results in real-time. None of the prior art mentioned above provides a method or device capable of performing real-time image separation for an unknown ensemble of materials that contains a large number of different materials.

SUMMARY OF THE INVENTION

A technique for inspecting and separating material-specific images from an unknown ensemble containing an arbitrary number of different materials, such as a passenger luggage or a piece of complicated equipment, in real-time is disclosed. The use of a real-time material-specific image separation device for security inspection or industrial structure inspection can greatly benefit the general public. For example, the capability of sorting out a plastic or wood gun hidden among items in a passenger's handbag can reduce the occurrence of aircraft hijacking. In the case of customs inspection, the capability of singling out specific materials from x-ray images can promote the efficiency of inspection and protect the general public. The present invention enables detection of, for example, illegal agricultural produce such as fruit, unreported precious metals such as gold, or controlled substances, such as plutonium, and suspiciously altered packaging structure for drug smuggling. In the case of aerospace nondestructive structural inspection, the present invention enables inspection of aluminum, steel, and special high temperature alloys of tungsten. The capability of separating the images from different metals can add efficiency in identifying and locating defects or cracks.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically.

The exponential attenuation of x-rays (or γ-rays) in materials is characterized by the so-called "mass attenuation coefficient" (unit: cm²/g) meaning the absorption cross-section per unit mass of material. The major physical contributions for this attenuation come from both photoelectron effect and Compton scattering. Therefore, between the range of 5 KeV and 8 MeV the mass attenuation coefficient is a function of photon energy and the electron density of materials. The "linear attenuation coefficient," μ (unit: cm$^{-1}$), can be obtained by multiplying the mass attenuation coefficient by the density (g/cm³) of the material. Using the linear attenuation coefficient, the attenuation of x-rays (or -y-rays) passing through a homogeneous material can be expressed as:

$$I(E,x,y) = I_o(E) \cdot e^{-\mu(E) \cdot T(x,y)} \quad (1)$$

where $I_0(E)$ is the incident photon intensity with photon energy E; I(E,x,y) is the measured intensity of x-ray (γ-ray) after passing through the material; T(x,y) is the thickness of the material along the straight line between the x-ray source and the detector point (x,y); and /x(E) is the linear attenuation coefficient of the material at photon energy E.

For an object containing N different attenuating materials in the x-ray field, the measured x-ray (or -y-ray) intensity at an image point (x,y) can be generally expressed as:

$$I(E,x,y) = I_0(E) \times e^{-(\sum_{j=1}^{N} \mu_j(E) T_j(x,y))} \quad (2)$$

where $I_0(E,x,y)$ is the incident intensity of photons directed toward the image point (x,y); $\mu_j(E)$ is the linear absorption coefficient of material j at the photon energy E; and $T_j(x,y)$ is the thickness of material j along the x-ray (or γ-ray) path between the source and the image point (x,y).

Figure 1:
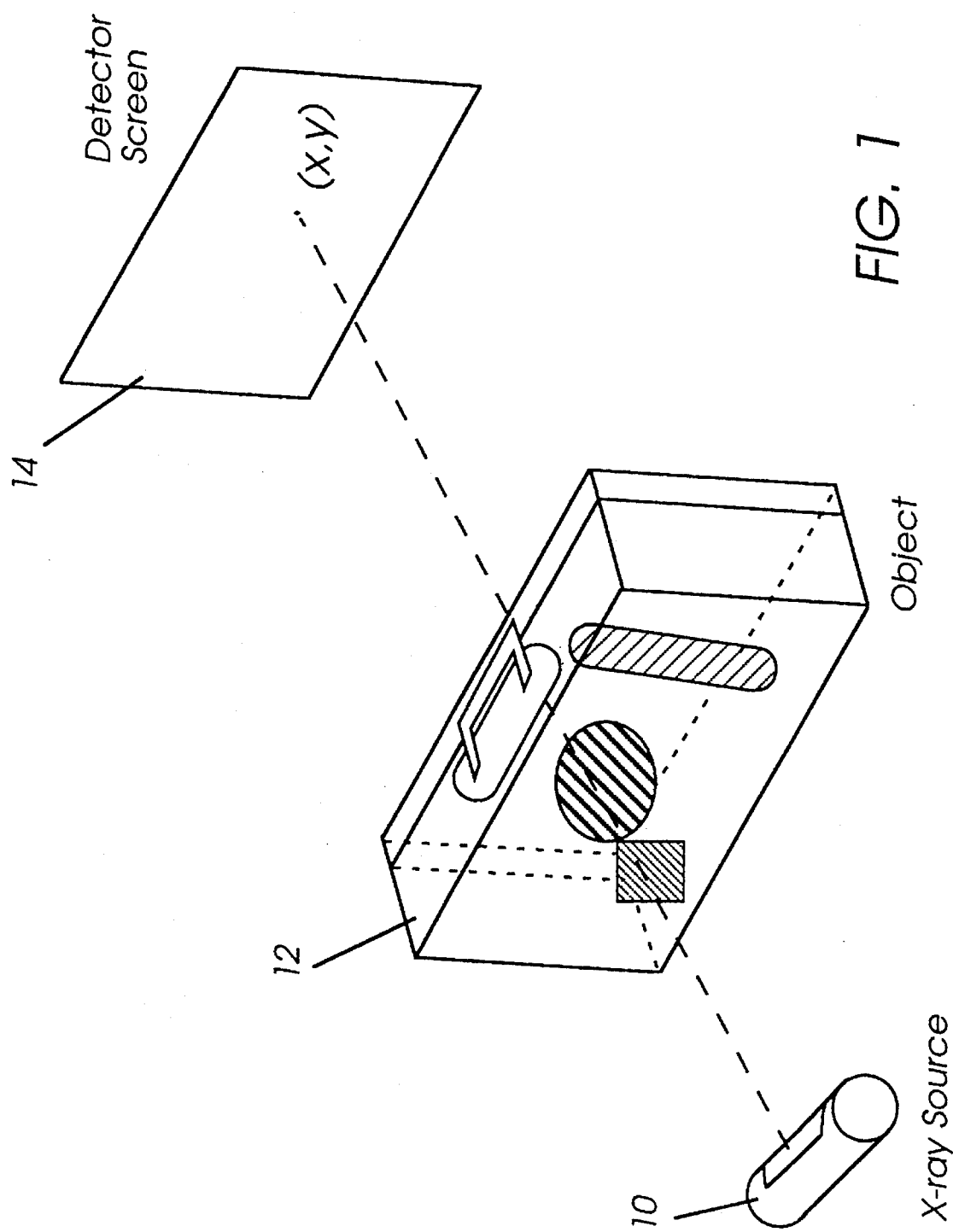
FIG. 1 shows an x-ray system applied to a luggage inspection environment.

FIG. 1 shows the geometrical relationship among the x-ray source 10, object 12, and the screen or detector point (x,y) 14. The measured intensity, I(E,x,y), has attenuation contributions From all the materials with their respective thicknesses along the x-ray (or γ-ray) path. Since I(E,x,y) is the measured intensity at the detector 14, the thickness as well as material information cannot be resolved by a single image at a single x-ray (or γ-ray) energy E.

If N different photon energies $E_k$, k=1 . . . N, are used separately to image the object under inspection, Equation (2) can be modified as:

$$I(E_k,x,y) = I_0(E_k) \times e^{-(\sum_{j=1}^{N} \mu_j(E_k) T_j(x,y))} \quad (3)$$

or $$I(E_k,x,y)/I_0(E_k) = e^{-(\sum_{j=1}^{N} \mu_j(E_k) T_j(x,y))} \quad (4)$$

where k=1 . . . N, and I(Ek,x,y) represents the measured x-ray (or γ-ray) intensity at incident photon energy $E_k$; $I_0(E_k)$ is the incident x-ray intensity at photon energy $E_k$; $\mu_j(E_k)$ is the linear attenuation coefficient of material j at the photon energy $E_K$; and $T_j(x,y)$ is the thickness distribution of material j along the x-ray path.

After taking natural logarithm on both sides of Equation (4) we can define the quantity $L_k(x,y)$ as:

$$\begin{aligned}& -\ln[I(E_k,x,y)/I_0(E_k,x,y)] \\ & \equiv L_k(x,y) \end{aligned} \quad (5)$$

$$= \left( \sum_{j=1}^{N} \mu_j(E_k) \times T_k(x,y) \right)$$

This equation can be written into the matrix form as:

$$\overline{L}(x,y) = \overline{\mu} \cdot \overline{T}(x,y) \quad (6)$$

where the matrix element/xik of the linear attenuation coefficient matrix $\overline{\mu}$ is the linear attenuation coefficient of material j at the photon energy $E_k$, i.e. $\mu_j(E_k)$.

The thickness distribution $T_j(x,y)$ of material j can therefore be solved by applying the inversion matrix of $\overline{\mu}$ on $\overline{L}(x, y)$:

$$\overline{T}(x,y) = \overline{\mu}^{-1} \cdot \overline{L}(x,y) \quad (7)$$

or explicitly, $$\begin{bmatrix} T_1(x,y) \\ T_2(x,y) \\ T_3(x,y) \\ \cdot \\ \cdot \\ \cdot \\ T_N(x,y) \end{bmatrix} = \begin{bmatrix} \mu_{11}^{-1} & \mu_{12}^{-1} & \mu_{13}^{-1} & \cdots & \mu_{1N}^{-1} \\ \mu_{21}^{-1} & \mu_{22}^{-1} & \mu_{23}^{-1} & \cdots & \mu_{2N}^{-1} \\ \mu_{31}^{-1} & \mu_{32}^{-1} & \mu_{33}^{-1} & \cdots & \mu_{3N}^{-1} \\ \cdot & \cdot & \cdot & & \cdot \\ \cdot & \cdot & \cdot & & \cdot \\ \cdot & \cdot & \cdot & & \cdot \\ \mu_{N1}^{-1} & \mu_{N2}^{-1} & \mu_{N3}^{-1} & \cdots & \mu_{NN}^{-1} \end{bmatrix} \times \begin{bmatrix} L_1(x,y) \\ L_2(x,y) \\ L_3(x,y) \\ \cdot \\ \cdot \\ \cdot \\ L_N(x,y) \end{bmatrix}, \quad (8)$$

where $\mu_{kj}^{-1}$'s are the matrix elements of $\overline{\mu}^{-1}$.

The solution $T_j(x,y)$, is the thickness distribution of the material j along the photon path between the source and detector point (x,y); and is therefore the projection image of material j.

If the mass attenuation coefficient $p_j$(unit: cm²/g), instead of the linear attenuation coefficient $\mu_j$, of material j is used, $d_j T_j$, instead of $T_j$, will be solved as the image information; where $d_j$ is the density of material j.

The image separation technique of the present invention does not depend on a specific form of photon generation or photon detection. The effect of the photon source comes from the quality of generated photon energy distributions and the available number of discrete photon energy distributions. This is manifested in the resultant material resolution in the final processed images.

All photons generated by a practical source can be approximated as a photon energy distribution that has a maximum intensity energy value and a finite band width. The larger the band width, the more likely the overlapping among photon energy distributions, the fewer the total number of available discrete photon energies, and the less the material resolution. The use of fewer discrete photon energies or larger bandwidth will reduce the capability of an imaging system to distinguish among materials that have attenuation coefficients close to each other. For example, with a conventional x-ray source it is difficult to distinguish nickel from iron, but it is easy to distinguish carbon from copper. In the case of using monochromized synchrotron radiation or nuclear decay sources, the better photon resolution and more available discrete photon energies will provide better material resolution.

According to the number of available discrete energies and the band width of the distribution, the materials can be sorted into several major groups according to the closeness of their attenuation coefficients at the available discrete photon energy distributions. Table 1 below shows the linear attenuation coefficients for carbon, nitrogen, oxygen, plastics, iron, nickel, copper, platinum, gold, and lead at photon energies from 40 KeV to 150 KeV. Carbon, nitrogen, oxygen, and plastics have similar linear attenuation coefficients over a wide range of photon energies; alloys of iron, nickel, and copper form a group; heavy metals such as platinum, gold, and lead form another group. The difference in linear attenuation coefficients among groups is of at least a factor of 10, and the difference between materials that belong to the same group is relatively small. These significant differences among groups and relatively small differences between the elements within the same group allow clear distinction of materials among groups even if the photon source is not ideally monoenergetic.

formed in real-time by a computer controlled or assisted arithmetic unit where the computer stores all the $\mu^{-1}$ matrices constructed prior to inspection. Tables of attenuation coefficients for various materials at different photon energies can be found in references such as "National Bureau of Standards Compilation of X-ray Crossections" by McMaster et al, University of California Livermore Report Number UCRL-50174, Section 11, Rev. 1 (1969).

The method of the image separation technique of the present invention is summarized as follows:

TABLE 1

UNIT = cm$^{-1}$

| Group | Light Nonmetal Elements | | | | Light Transition Metals | | | Heavy Metals | | |
|---|---|---|---|---|---|---|---|---|---|---|
| Material | Carbon | Nitrogen | Oxygen | Plastics | Iron | Nickel | Copper | Platinum | Gold | Lead |
| 40 KeV | 0.25 | 0.28 | 0.31 | 0.26 | 27.9 | 40.0 | 42.5 | 263.6 | 246.5 | 159.7 |
| 50 KeV | 0.23 | 0.24 | 0.26 | 0.24 | 15.0 | 21.3 | 22.8 | 146.2 | 137.2 | 89.1 |
| 60 KeV | 0.21 | 0.22 | 0.23 | 0.23 | 9.2 | 13.0 | 13.9 | 90.5 | 85.3 | 56.5 |
| 70 KeV | 0.20 | 0.21 | 0.22 | 0.22 | 6.2 | 8.7 | 9.3 | 60.6 | 57.1 | 37.3 |
| 80 KeV | 0.19 | 0.20 | 0.20 | 0.21 | 4.6 | 6.3 | 6.7 | 187.7 | 40.7 | 26.6 |
| 90 KeV | 0.19 | 0.19 | 0.19 | 0.20 | 3.6 | 4.8 | 5.1 | 138.0 | 128.2 | 80.7 |
| 100 KeV | 0.18 | 0.18 | 0.19 | 0.19 | 2.8 | 3.8 | 4.0 | 104.7 | 98.6 | 62.2 |
| 110 KeV | 0.18 | 0.18 | 0.18 | 0.19 | 2.4 | 3.2 | 3.3 | 81.5 | 77.8 | 49.1 |
| 120 KeV | 0.17 | 0.17 | 0.17 | 0.18 | 2.1 | 2.7 | 2.8 | 65.1 | 62.5 | 39.6 |
| 130 KeV | 0.17 | 0.17 | 0.17 | 0,18 | 1.9 | 2.4 | 2.5 | 52.9 | 51.1 | 32.4 |
| 140 KeV | 0.16 | 0.16 | 0.16 | 0.17 | 1.7 | 2.1 | 2.2 | 43.9 | 42.5 | 26.9 |
| 150 KeV | 0.16 | 0.16 | 0.16 | 0.17 | 1.5 | 1.9 | 2.0 | 36.8 | 35.7 | 22.7 |

The representative linear attenuation coefficients for a group can be approximated by averaging among the photon energy distribution and the reasonably assumed material composition. The relatively small differences in linear attenuation coefficients within a group will allow a wide range of possible material weightings in the averaging process. To perform real-time image separation, the possible materials existing in the inspection can be previously grouped according to the closeness of their linear attenuation coefficients at the chosen different x-ray energy distributions where the selection of x-ray energy is based on the source capability and is such that the chosen x-ray distributions have minimal possible mutual overlappings. After such grouping procedure, a representative linear attenuation coefficient $\mu_{jk}$ for a group j of material can then be reasonably calculated for each chosen x-ray energy distribution $E_k$. The total number of material groups that can be distinguished is equal to the total number of photon energies used.

The matrix $\mu^{-1}$ can be obtained by first constructing the linear attenuation coefficient matrix $\mu$ with the calculation of the representative group linear attenuation coefficient $\mu_{jk}$ for each group at each x-ray energy distribution, and then solving for the inversion of $\mu$. This $\mu^{-1}$ is an N by N matrix where N is the total number of material groups and also the total number of x-ray energies used. Different $\mu^{-1}$ matrices for different possible sets of material groups that may exist in an inspection can be previously constructed and stored in the inspection system. If a certain presumed $\mu^{-1}$ matrix does not give the best separation of material-specific images during the inspection, other $\mu^{-1}$ matrices can be switched in one by one until the best separation result, or the best determination of existing material groups in the ensemble under inspection, is reached. Practically, such a task of dynamically switching between $\mu^{-1}$ matrices can be per- 1. According to the characteristics and capabilities of the photon source, decide the available discrete x-ray energies or distributions to be used for imaging. The photon energy distribution after appropriate filtration should be included in the consideration. A reasonable range for conventional x-ray source is from 60 to 200 kVp.
2. According to 1 and the possible materials existing in the inspection, sort these materials into several groups according to the closeness of their linear attenuation coefficients at the chosen photon energy distributions. Find the representative linear attenuation coefficients for each group at different photon energy distributions.
3. Construct the matrices $\mu$'s for all possible combinations of material groups existing in the ensemble and its inversion, $\mu^{-1}$, where the matrix element of $\mu$, $\mu_{jk}$, is given by the representative linear attenuation coefficient of the material group j at the photon energy distribution $E_k$. The dimension of the matrix is determined by the total number of available or chosen photon energy distributions.
4. Acquire images at the chosen photon energies in 1 and digitize the images. The combination of camera aperture and x-ray tube charge (mAs) is such that the maximum intensity does not saturate the x-ray detector or camera output. The incident fluence $I_0(E_k)$ for each photon energy is also measured at this stage.
5. Perform arithmetic operation on the digitized images from 4 on a pixel-by-pixel basis. This step at least includes taking natural logarithm of the images as described in Equation (5) and the arithmetic operation as described by Equation (8). The images of each material group, $T_j(x,y)$, can be obtained at this stage.
6. Maximize and display the images $T_j(x,y)$. Maximization means the mathematical manipulation of images $T_j(x,y)$ so that the visual display on the monitor screen is best for inspectors.

It is preferable to use a computer controlled digital imaging system, in which the main computer controls system timing and data flow, and also calculates and stores preinspection information such as matrix elements of $\mu^{-1}$ for fast image processing. For the purpose of arithmetic operation, hardware look-up tables and independent image processors are used in the circuitry. The procedure described above is alterable according to detailed hardware settings; for example, steps 4 through 6 can also be performed with analog arithmetic circuitry without affecting the separation of material specific images.

Figure 2:
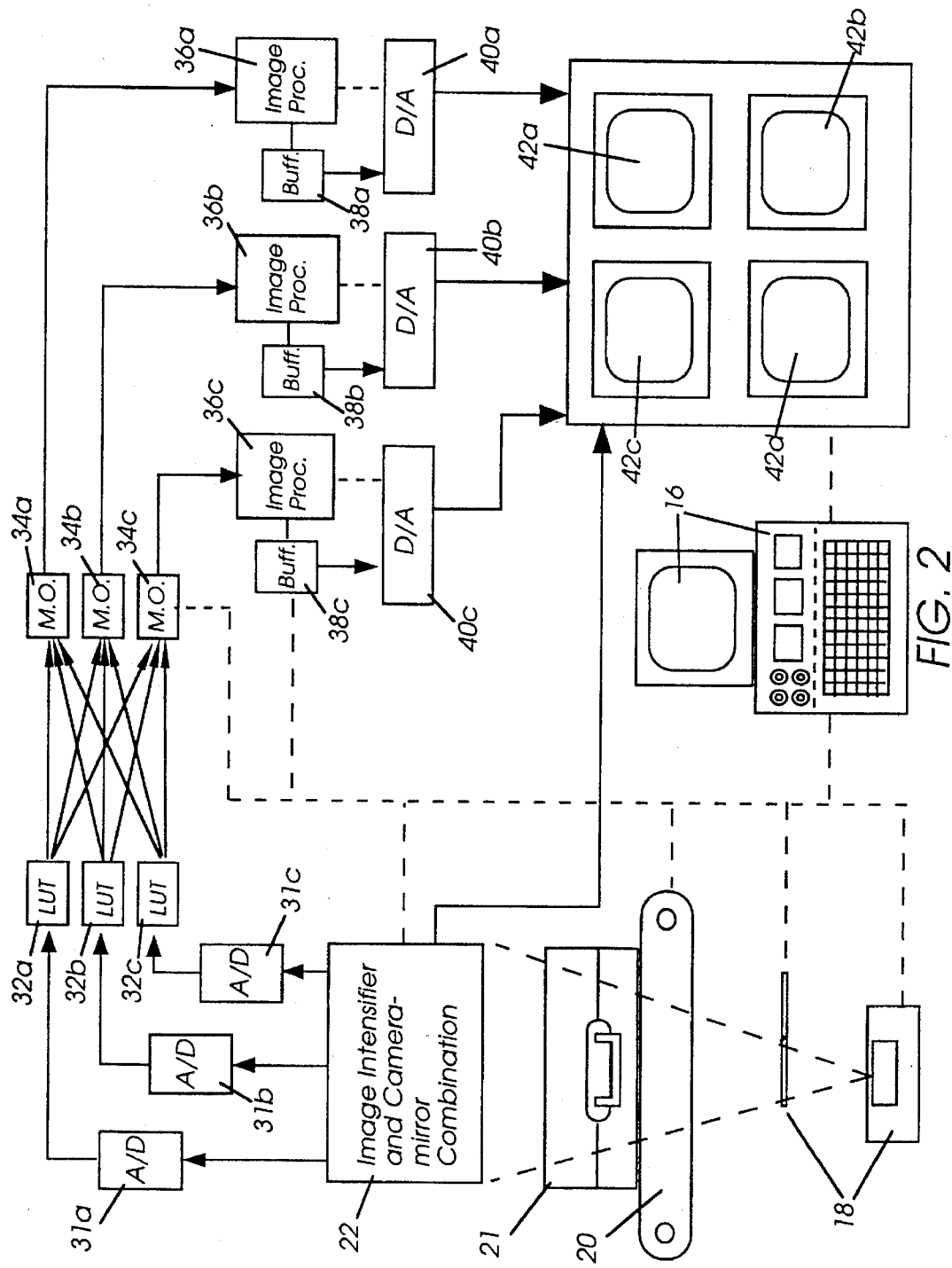
FIG. 2 shows the luggage inspection system of the presently preferred embodiment.
Figure 3:
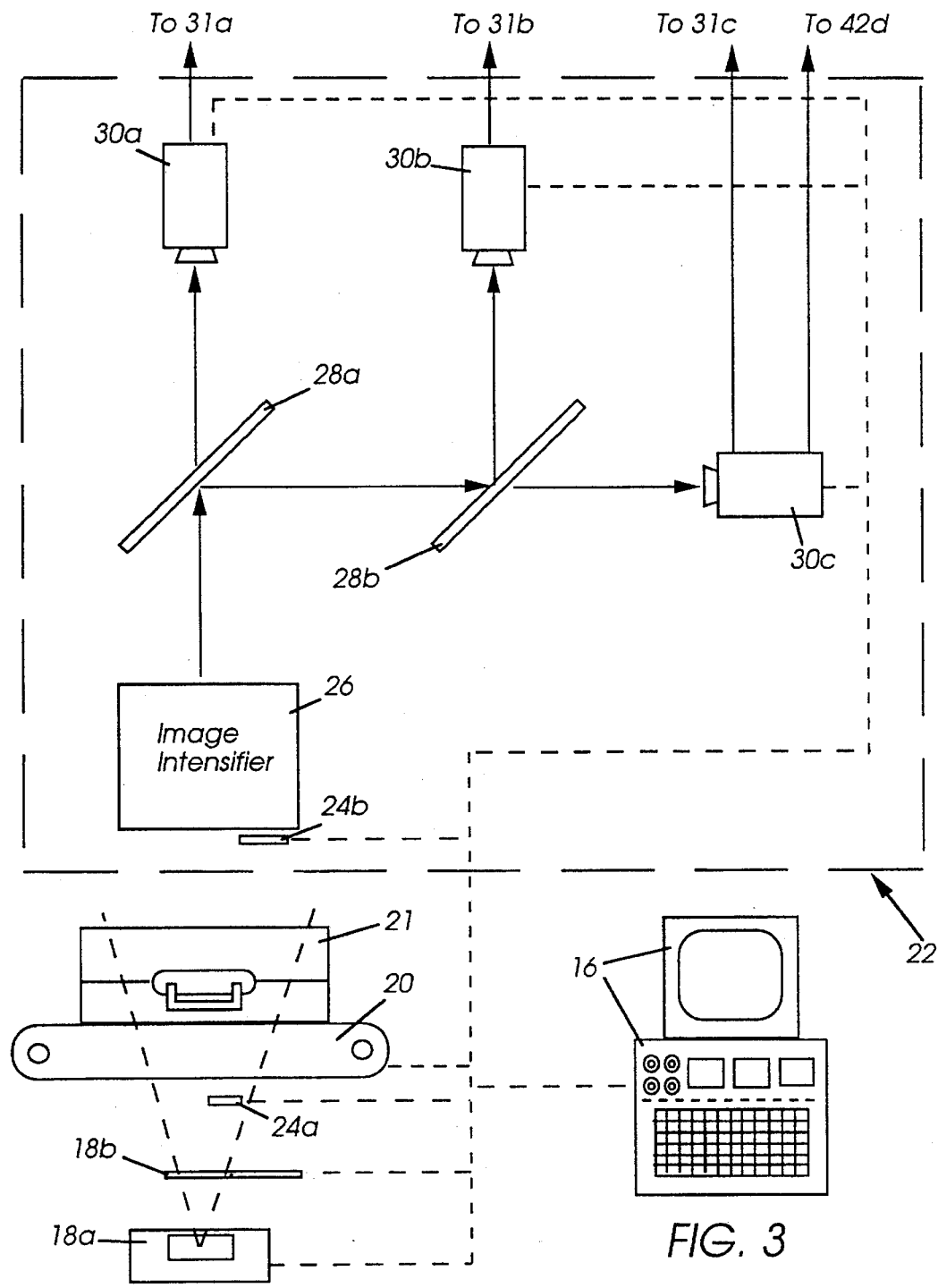
FIG. 3 illustrates the image intensifier and the camera mirror assembly of the presently preferred embodiment.

The presently preferred embodiment is herein given in the form of a luggage inspection system, yet it is extendable to other non-destructive inspection systems. FIGS. 2 through 5 describe a system which provides real-time material-specific image separation for three or more major material groups mentioned earlier. The disclosed system is readily changeable into a system capable of performing material-specific image separation tasks for N major material groups by adding more image acquisition and processing channels, which is described in FIG. 2. In FIGS. 2 and 3 the solid lines with arrows represent the flow of image data; and the thick dashed lines represent the control or feedback data lines.

The luggage inspection system of the presently preferred embodiment is shown FIG. 2. A main computer 16 provides general control of the system. The x-ray target and filter assembly 18 provides the different x-ray photon energies needed for the image separation operation. The conveyor belt mechanism 20 transports luggage into the x-ray field. The image intensifier and camera-mirror assembly 22 detects and converts x-ray information into video images. Also contained in this assembly 22 are the ionization cells which provides the x-ray fluence measurement and feedback control functions. The analog-to-digital (A/D) conversion devices 31a, 31b, and 31c convert the analog low, medium, and high energy images, respectively, from the image intensifier assembly 22 into digital images. The logarithmic look-up table devices 32a, 32b, and 32c perform logarithmic operations on the digitized images output from analog-to-digital converters 31a, 31b, and 31c. These devices 32a, 32b, and 32c may include digital frame buffers as well. The matrix operation devices 34a, 34b, and 34c perform matrix operations on the logged images from the logarithmic look-up tables 32a, 32b, and 32c. The image processors 36a, 36b, and 36c maximize the results from the matrix operation devices 34a, 34b, and 34c for display. The dual port video buffers 38a, 38b, and 38c and video digital-to-analog (D/A) converters 40a, 40b, and 40c store and convert the digital images into analog video signals for the display monitors 42a, 42b, and 42c.

The luggage inspection system of the presently preferred embodiment is designed to distinguish among three major groups of materials as described previously: light nonmetal materials such as plastics; lighter metals such as iron and copper; and heavy metals such as gold and platinum. It can be easily modified for the situation of using more than three discrete photon energies, as well as using only two different photon energies. The x-ray source 18a of FIG. 2 generates three discrete photon distributions which are modified by filters for small overlappings.

Before inspection, the $\mu^{-1}$ matrix previously mentioned in Equations (7) and (8) is constructed using control computer 16 software according to the chosen photon distributions and the material groups under inspection. The values of the appropriate matrix elements are then transferred and stored into the matrix operation devices 34a, 34b, and 34c, respectively, for fast arithmetic operations during the real-time data acquisition. The $\mu^{-1}$ matrix will remain the same until the assumed material groups under inspection have changed.

In case it is necessary to separate images of specific material from groups such as the 4d transition metals that have linear attenuation coefficient values lying between the light metals and heavy metals, the appropriate $\mu^{-1}$ matrix can be constructed by the control computer 16 and quickly loaded into matrix operation devices 34a, 34b, and 34c. A convenient mode of operation is to previously construct different $\mu^{-1}$ matrices corresponding to all reasonable combinations of photon energies and material groups and to save the values in the control computer 16. It is then easy to change the inspection mode by loading the $\mu^{-1}$ matrices into the matrix operation devices 34a, 34b, and 34c.

The control computer 16 controls the system timing including that for the x-ray source and filter assembly 18 and the on/off control of CCD (Charge-Coupled Device) cameras embedded in the image intensifier and camera-mirror combination 22. The control timing signal is generated by circuits interfaced to and controlled by the computer 16. The data acquisition mode can be changed by switching between different prestored timing setups on the computer 16. During the inspection, the control computer 16 can manage the continuation or interruption of the conveyor belt mechanism 20 as demanded by the inspector or special electrical and/or mechanical conditions.

The control computer 16 also stores the preinspection calibration data acquired with the ionization cells 24a and 24b shown in FIG. 3. The calibration data acquired with ionization cell 24a is used in the form of a look-up table to provide instantaneous and accurate determinations of the incident intensity $I_0(E)$ at different photon energies. The calibration data acquired with ionization cell 24b is also used in the form of a look-up table to provide instantaneous feedback control information to the main computer 16, x-ray source 18a, and the camera apertures in 30a, 30b, and 30c so that the output gray levels from the cameras 30a, 30b, and 30c are not saturated or undersaturated.

Before the start of data acquisition, the following two steps are completed. First, the previously defined $\mu^{-1}$ matrices are constructed for three material groups and stored in the appropriate memory area. Secondly, the incident photon intensity and camera saturation level as can be measured with the ionization cells 24a and 24b embedded in the image intensifier and camera-mirror assembly 22 is calibrated, and the calibration data is stored in the form of look-up tables for instantaneous arithmetic and feedback control operations.

The details for the operation of the x-ray source assembly 18 and image intensifier and camera-mirror assembly 22 are now described with reference to FIGS. 3 and 4. Turning now to FIG. 3, the control computer 16 was described previously. The conveyor belt mechanism 20 transports the luggage 21 into the x-ray field. A conventional x-ray source 18a preferably contains a rotating anode target, and its filament emission and target kVp settings are controlled by the control computer 16. An x-ray filter assembly 18b carries different filter disks for different x-ray energy distributions. Two ionization cells 24a and 24b provide calibrated incident x-ray fluence measurements (cell 24a) and saturation feedback controls for CCD cameras (cell 24b). An image intensifier 26 converts x-ray intensity proportionally into visible or detectable light for the CCD cameras 30a, 30b, and 30c. Two parallel mirrors 28a and 28b are used for splitting the visible light from the image intensifier 26 into three CCD cameras 30a, 30b, and 30c. The CCD cameras 30a, 30b, and 30c are designated for the detection of low, medium, and high energy images, respectively.

The x-ray source 18a is sequentially activated in the fashion of Low-Medium-High, while the corresponding filter section of the filter assembly 18b is switched into the x-ray field accordingly. (This process is described later with reference to FIGS. 4a and 4b.) The incident photon intensity at different energies $I_0(E_k)$ is measured by the ionization cell 24a and instantaneously converted into $\ln(I_0(E_k))$ by the previously-constructed look-up table and then stored in the buffer area of the logarithmic and arithmetic devices 32a, 32b, and 32c (FIG. 2) for later use. After the image intensifier stage 26, the generated visible light that carries the image information is split into three beams by the two parallel mirrors 28a and 28b. The transmission and reflection ratio of the mirror 28a is chosen such that mirror 28a has 33.5 percent transmission toward camera 30a and 66.5 percent reflection toward the other mirror 28b. The mirror 28b is chosen to have 50 percent transmission and 50 percent reflection. Such choice will generate a light input intensity ratio among the three CCD cameras 30a, 30b, and 30c as 33.50: 33.25: 33.25, which is approximately equal.

The enable/disable timing of CCD camera frame capture is synchronized with the x-ray source 18a such that when the low energy is turned on, the camera 30a is enabled with cameras 30b and 30c disabled; when the medium energy is turned on the camera 30b is enabled with cameras 30a and 30c disabled; and when the high energy is turned on, the camera 30c is enabled with cameras 30a and 30b disabled. Thus, cameras 30a, 30b, and 30c are assigned to low, medium, and high image acquisition energies, respectively. The purpose of this multiple camera-mirror combination is to save time that would otherwise be wasted in waiting for the downloading and digitization of the previous frame in the case of a one-camera operation. Accordingly, the three CCD cameras operate in a semiparallel fashion. An analog image signal can be connected out of either the medium-energy camera 30b or the high-energy camera 30c for direct analog display on the monitor 42d (FIG. 2). This image on monitor 42d is the same as a conventional single energy band projection x-ray image, and provides an original view including all of the materials.

Figure 4A:
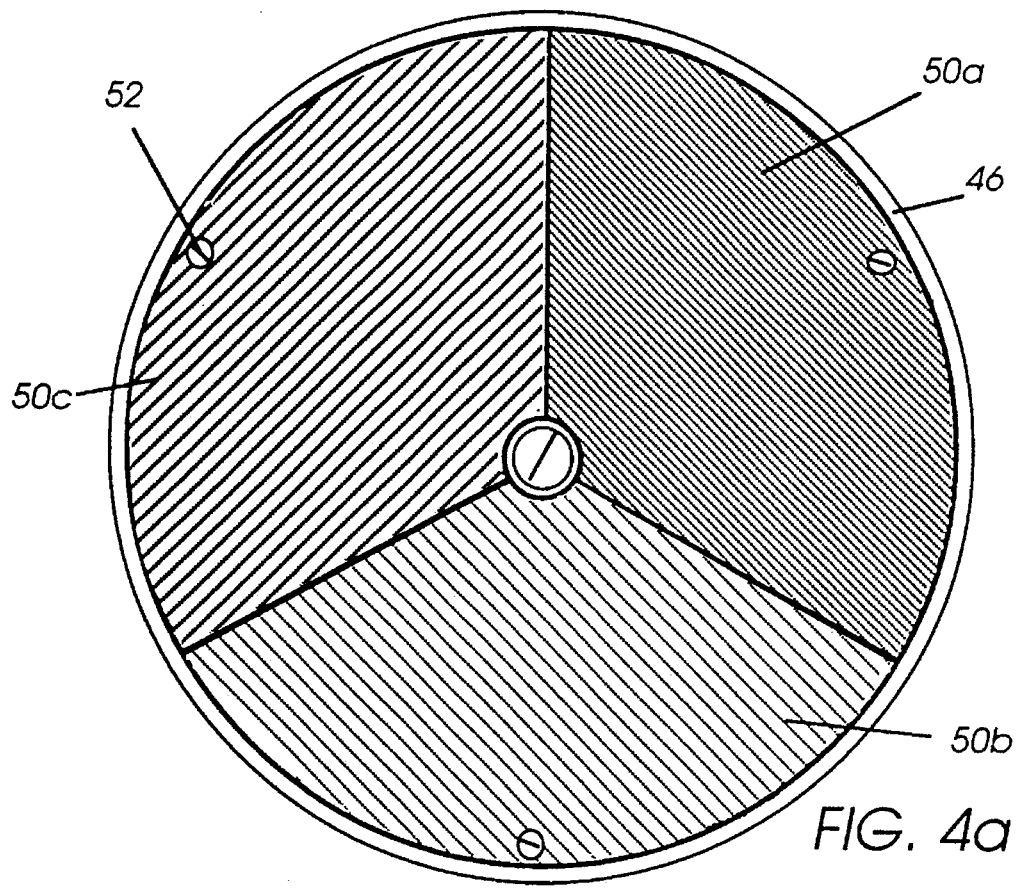
FIGS. 4a and 4b the x-ray filter design of the presently preferred embodiment.
Figure 4B:
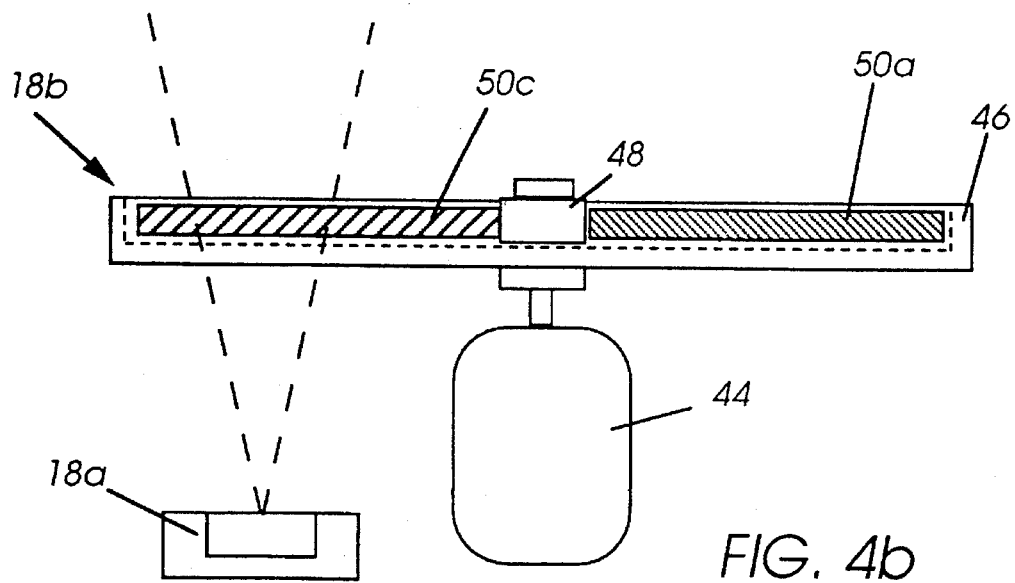

The filter assembly 18a of the presently preferred embodiment is shown in FIGS. 4a and 4b. A stepping motor 44 rotates a circular aluminum or strong plastic tray 46 that is fixed on the motor axle 48. Several filter sections 50a, 50b, and 50c are secured to the filter tray 46. The angular span of each section is $2\pi/N$, where N is the total number of filter sections and also the different x-ray energies used. Each of the individual filter sections can be previously chosen and screw-mounted 52 on the filter tray 46. The material and thickness of each of the filter sections 50a, 50b, and 50c is determined according to the x-ray energy. The principles of choosing appropriate filters at each energy can be found in books such as "The Physics of Radiology," 4th Edition, by H. E. Johns and J. R. Cunningham (Charles C. Thomas, Publisher, 1983).

With the camera-mirror combination 28a, 28b, 30a, 30b, and 30c (FIG. 3) and the appropriate on/off timing of each camera as described previously, the three cameras 30a, 30b, and 30c operate independently in the acquisition of images generated from their respectively assigned x-ray energies. Looking at camera 30a that is assigned to the low-energy frames, for example, after the acquisition of each image frame the CCD camera 30a starts to send the analog image out of its buffer memory to the analog-to-digital converter 30a. This operation does not depend on the status in the other two data channels processed by CCD cameras 30b and 30c. After the analog-to-digital conversion is performed by analog-to-digital converter 31a, the digital data is sent to the hardware logarithmic and arithmetic device 32a. The natural logarithm of the data is first taken, and the result is then subtracted from the measured value $\ln(I_0(E_k))$. The quantity $L_k(x,y) \equiv \ln(I(E_k,x,y)/I_0(E_k))$ is thus obtained. This logarithmic and arithmetic operation step is independent of the other two channels processed by CCD cameras 30b and 30c in terms of data flow.

After the logarithmic and arithmetic stage 32a, the data in each energy channel is sent to the matrix operation 34a, 34b, and 34c. The mathematical operations taking place in these matrix operation devices 34a, 34b, and 34c can be expressed by the following equations:

$$34a: T_{N-M} = \mu^{-1}_{N-M,Low} \cdot L_{Low} + \mu^{-1}_{N-M,Med} \cdot L_{Med} + \mu^{-1}_{N-M,High} \cdot L_{High} \quad (9)$$

$$34b: T_{L-M} = \mu^{-1}_{L-M,Low} \cdot L_{Low} + \mu^{-1}_{L-M,Med} \cdot L_{Med} + \mu^{-1}_{L-M,High} \cdot L_{High} \quad (10)$$

$$34c: T_{H-M} = \mu^{-1}_{H-M,Low} \cdot L_{Low} + \mu^{-1}_{H-M,Med} \cdot L_{Med} + \mu^{-1}_{H-M,High} \cdot L_{High} \quad (11)$$

In these three equations, T represents the thickness distribution and the indexes N–M, L–M, and H–M stand for the groups of light nonmetals, light metals, and heavy metals, respectively. The $\mu^{-1}_{j,k}$ quantities are the matrix elements of the inverted linear attenuation coefficient matrix $\mu$ previously mentioned in Equations (6) through (8), and the matrix $\mu^{-1}$ is constructed are stored previous to the start of inspection. The quantities $L_{Low}$, $L_{Med}$, and $L_{High}$) are the previously mentioned logarithmically and arithmetically processed images which are acquired at low, medium, and high x-ray energies, respectively.

Taking the light nonmetal group as an example, the $L_k$'s (i.e. $L_{Low}$, $L_{Med}$, and $L_{High}$) obtained from the logarithmic and arithmetic devices 32a, 32b, and 32c are all input to the board 34a, and each of the three $L_k$'s is then multiplied by the corresponding matrix element of $\mu^{-1}$ as specified in Equation (9). The thickness distribution for the light nonmetal material, $T_{N-M}(x,y)$, is then obtained.

During this operation, the system cannot take any matrix operation until the high energy, or the last, frame in the low-medium-high x-ray sequence is taken. In order to save the wait time, the matrix operation can be processed on a pixel-by-pixel basis. That is, as soon as the value for the first pixel from high energy image frame arrives, the matrix operation for that pixel is executed.

In the case that the initially chosen $\mu^{-1}$ matrix cannot achieve the material-specific image separation as expected, the operator can try other existing $\mu^{-1}$'s by switching in the memory location matrix elements of the new $\mu^{-1}$ to the appropriate memory of the matrix operation device 34a, 34b, 34c instantaneously. A convenient way for dynamic switching of $\mu^{-1}$ is to use control software to perform the switching automatically and interrupt the switching while a good image separation is observed on the screen.

The image separation is basically completed after processing by the matrix operation devices 34a, 34b, and 34c. The image obtained after these matrix operations, however, may not be at its maximum display state in terms of contrast and brightness. The image processors 36a, 36b and 36c are therefore used to provide for a maximum display. The algorithm implemented by these image processors 36a, 36b, and 36c is previously determined and programmed. The video buffer memory units 38a, 38b, and 38c and the digital-to-analog (D/A) converters 40a, 40b, and 40c are controlled by the image processors 36a, 36b, and 36c, respectively, to feed maximized images to the analog video displays 42a, 42b, 42c, and 42d. In the presently preferred embodiment, the images of the different groups are independently processed and displayed from elements 34 to elements 42, and the lag between material images is small due to the highly parallel processing. Finally, the separated image for each group is displayed on the monitors 42a, 42b, and 42c, respectively, while the image that includes all of the materials is displayed on monitor 42d, as mentioned earlier.

According to the real-time monitor disclosed herein, a luggage inspector can watch a continuous stream of objects passing by on a conveyor belt, for example, and immediately distinguish among three groups of materials contained in the object under inspection. The inspector can operate the system in the conventional mode (i.e. continuous display of mixed material image), and can decide when to interrupt this mode to perform image separation as needed. In the conventional mode the x-ray source is put on medium or high energy and image processing steps 30 through 40 are skipped. Additionally, only monitor 42d operates to display an image of all the materials. When the image separation task is needed, the inspector uses the control computer 16 to execute the image separation mode of operation as described previously.

The components described in the preferred embodiment can be modified according to the inspection needs and available technologies. One important feature of the above-disclosed embodiment is the use of the camera-mirror combination 28a, 28b, 30a, 30b, and 30c (or other equivalent light distributing mechanism) to separate the acquisition and processing of images at different energies. Similar designs are easily adaptable to process images for either more than three x-ray energies or two different energies.

Figure 5A:
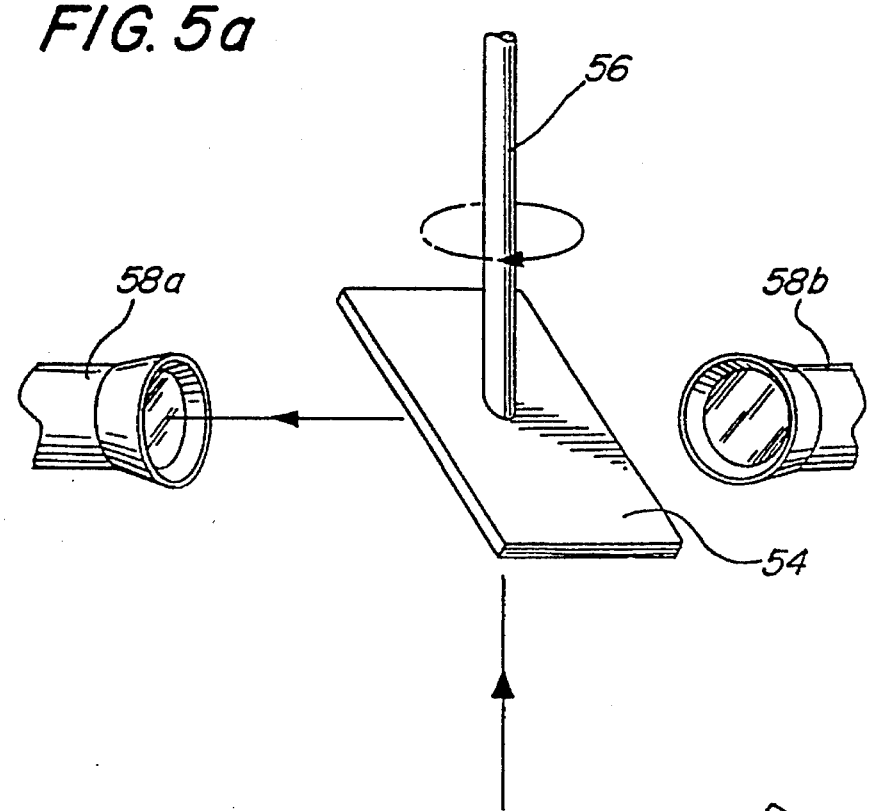
FIGS. 5a and 5b illustrate a camera mirror setup according to an alternative embodiment.
Figure 5B:
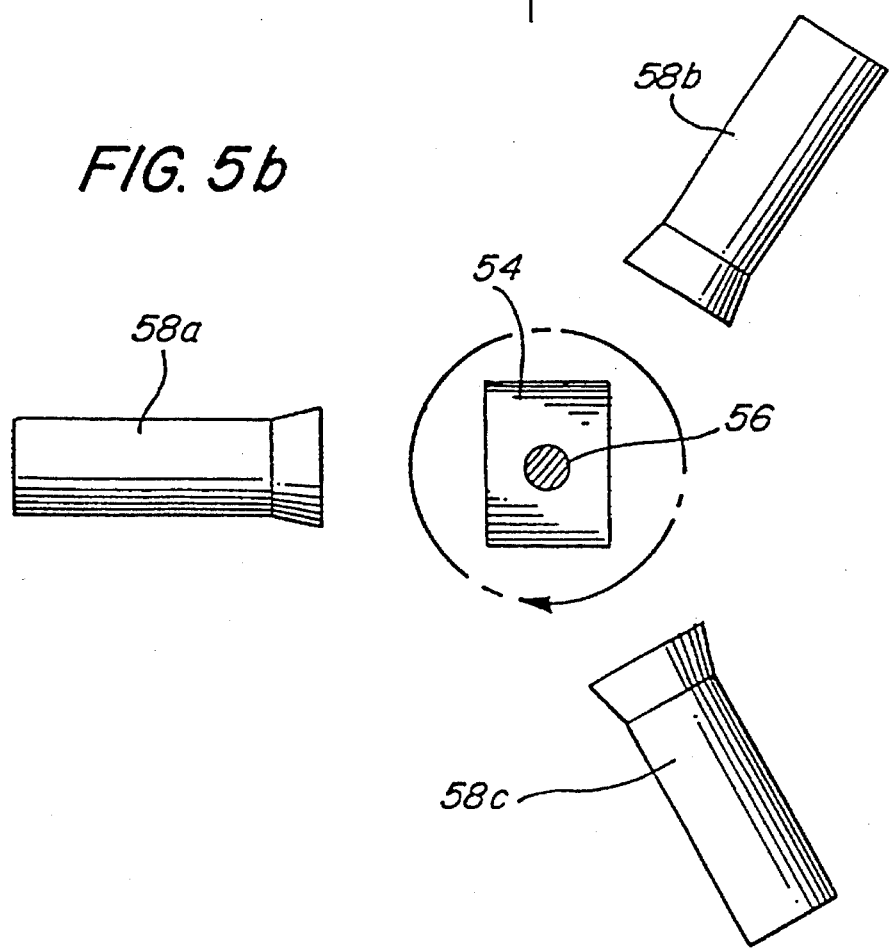

An alternative embodiment of the camera-mirror configuration 28a, 28b, 30a, 30b, and 30c described in FIG. 3 is shown in FIGS. 5a and 5b. A 100 percent reflection mirror 54 is shaft-mounted 56 preferably onto a stepping motor (not shown) which has a timing sequence such that the mirror stops in front of one of the three CCD camera 58a while the corresponding x-ray energy level is turned on. After the x-ray is turned off, the motor moves the mirror to the next camera 58b and so forth.

The use of image intensifier 22 is not mandatory because varieties of semiconductor based plain x-ray detectors are being developed and tested. In such an embodiment, the image intensifier 22 is omitted, and the fiber optics arrays may be used to derive and split the image signals for processing.

Figure 6:
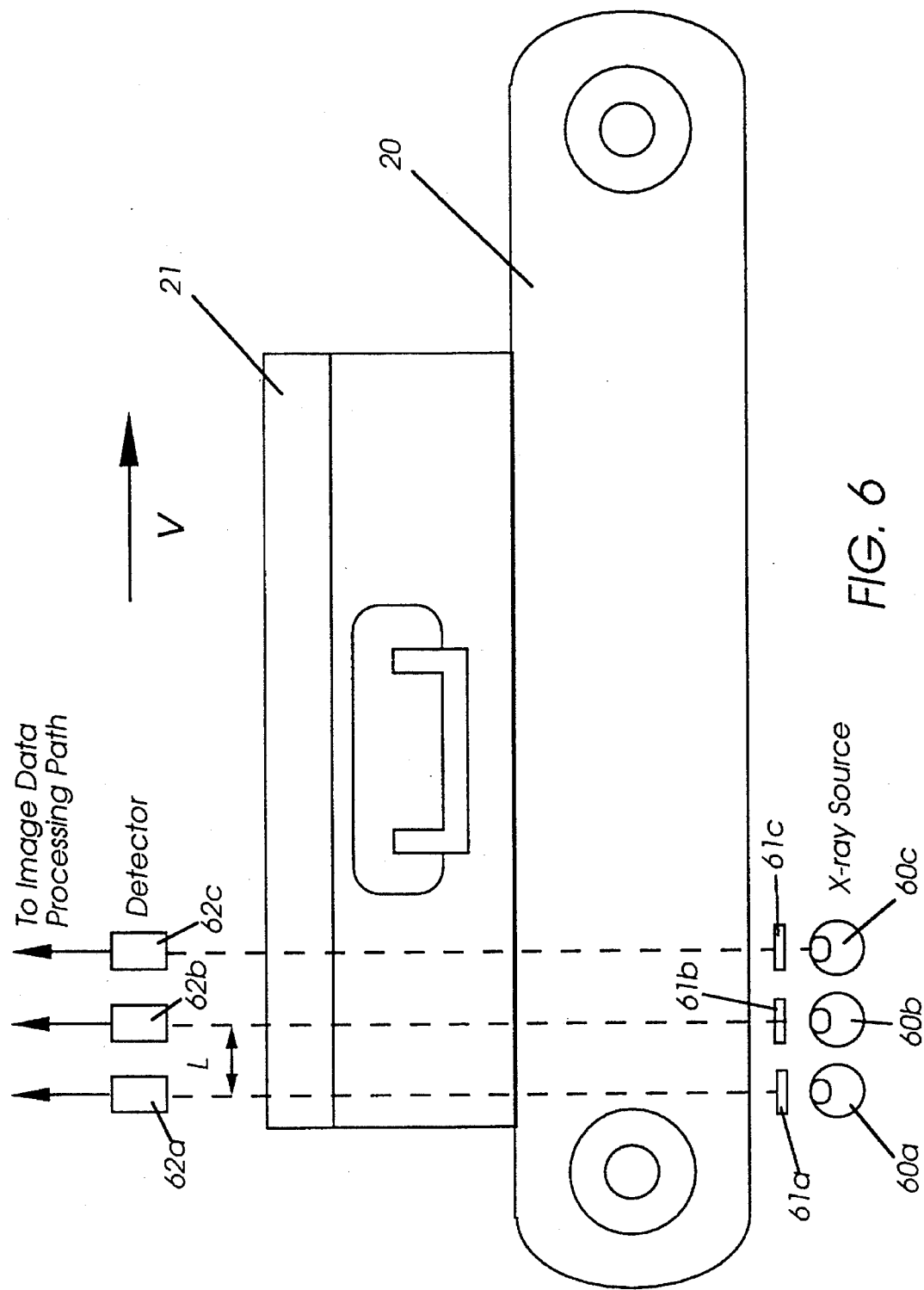
FIG. 6 illustrates an x-ray source detector portion according a second preferred embodiment.

Another preferred embodiment for the x-ray source-detector portion is illustrated in FIG. 6. Three x-ray fan beams (as opposed to x-ray projection imaging, described above) carrying photon energies of low, medium, and high, respectively, are generated by sources 60a, 60b, and 60c and by filters 61a, 61b, and 61c. The corresponding x-ray detectors are located at 62a, 62b, and 62c with transverse separation length L as shown in the figure. After processing by detectors 62a, 62b, and 62c, the transmitted x-ray information for each energy is converted and sent into the image processing route beginning at 30a, 30b, and 30c in FIG. 2. This setup provides simultaneous and independent image acquisition for the three different x-ray energies, thereby enabling real-time image processing. If the conveyer belt 20 is moving with speed $\bar{v}$, the time lag between the first (60a and 61a) and second (60b and 61b) or the second (60b and 61b) and the third (60c and 61c) source-detector pairs for the same location on the object 21 can be expressed as $\Delta T=L/|\bar{v}|$. Even if the conveyor belt has uneven motion, this time lag can be feedback-corrected and will only affect the onset time of the first material-specific image frame and will not affect the subsequent, overall real-time imaging operation.

One advantage of this multiple source scanner in terms of performing real-time imaging is that the total number of source-detector pairs does not limit the real-time performance, while the conventional single-source scanner is limited by the total number of different x-ray energies to be generated and the length of each x-ray generation pulse. The frame acquisition rate for a conventional single-source scanning device is limited by the time spent in waiting for all the images from the different energies to be acquired.

Figure 7:
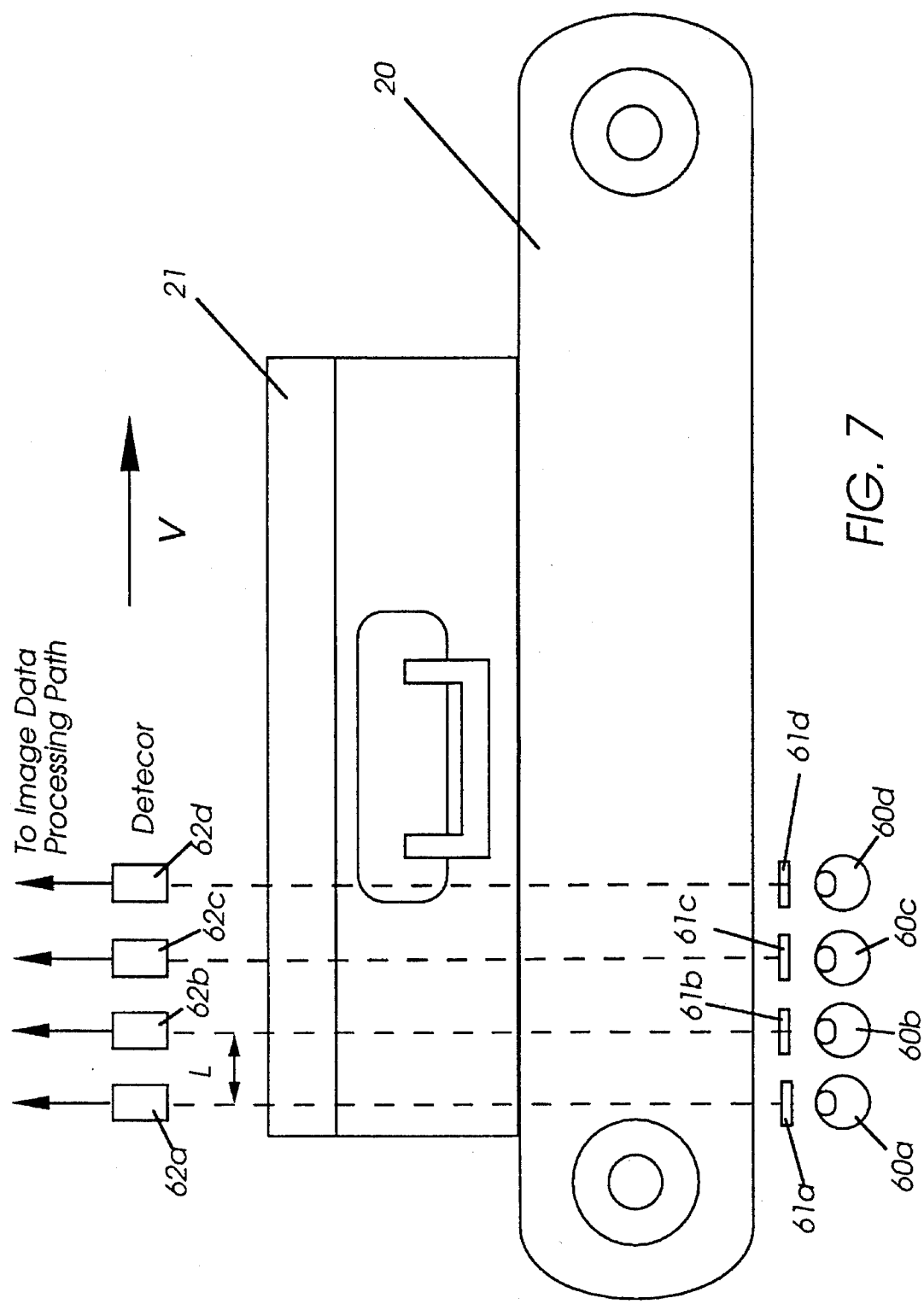
FIG. 7 illustrates a scanning system with four x-ray source detector pairs according to a third preferred embodiment.
Figure 8A:
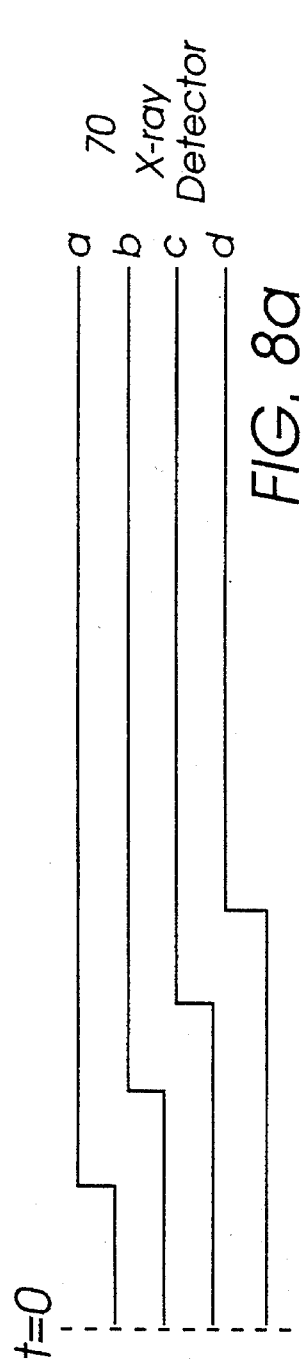
FIGS. 8a through 8f are timing diagrams for the multiple source scanning system according to an alternative embodiment.
Figure 8B:
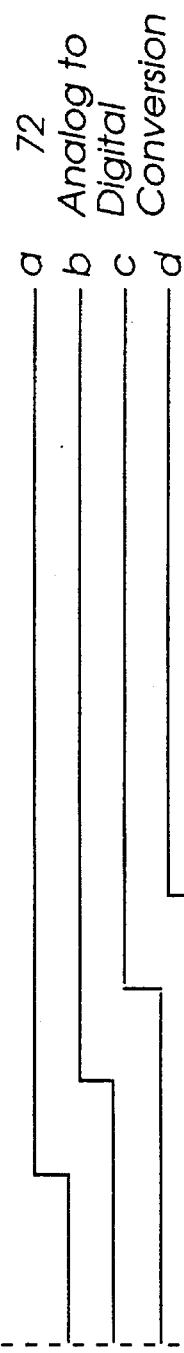
Figure 8C:
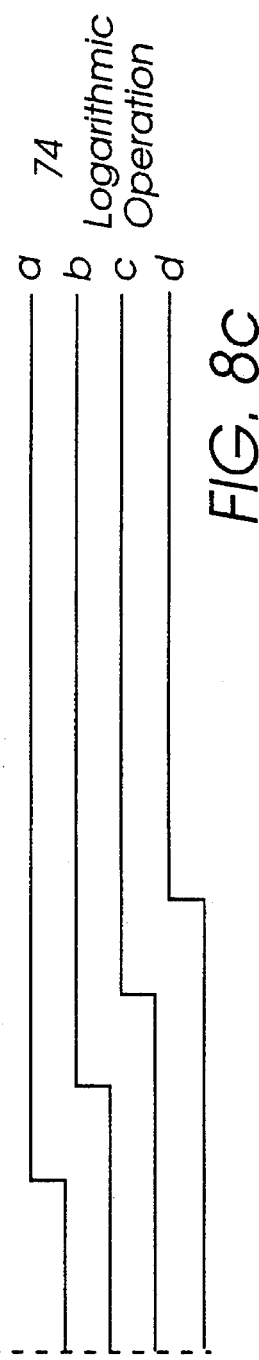
Figure 8D:
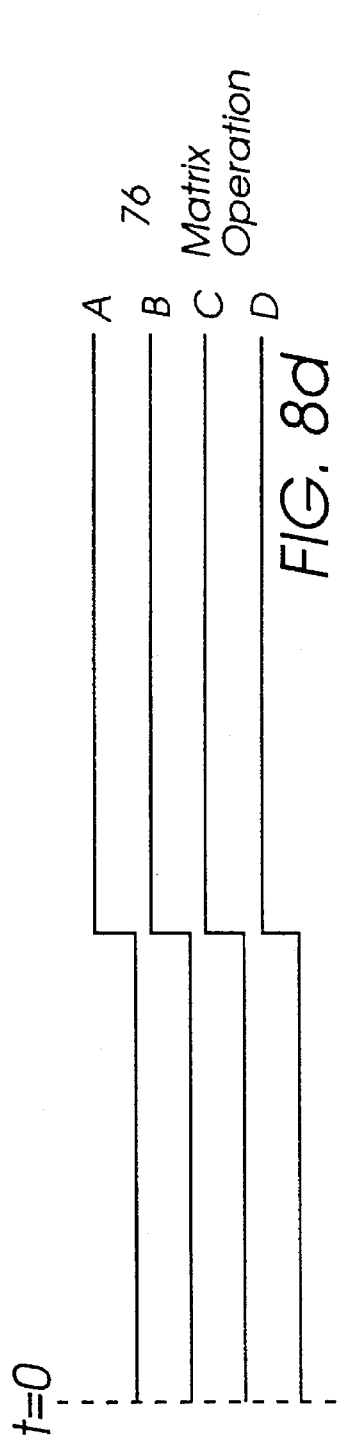
Figure 8E:
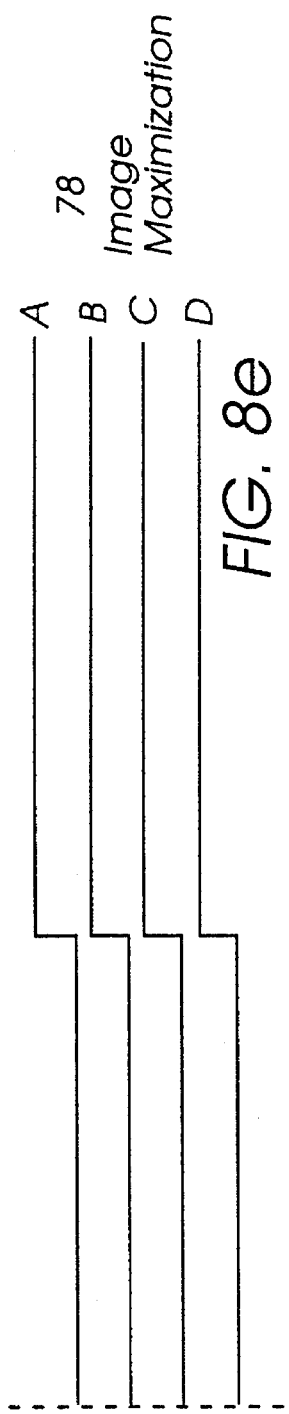
Figure 8F:
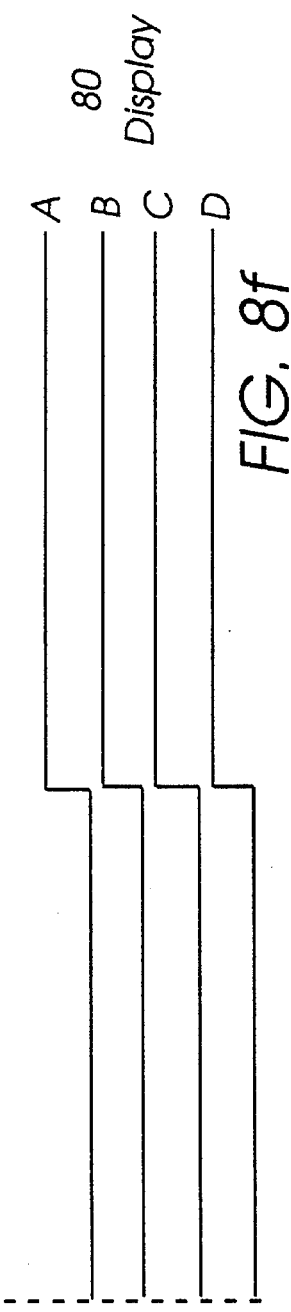

FIG. 7 shows a scanning system with four x-ray source-detector pairs capable of separating four groups of materials such as light nonmetals, light and 3d transition metals, 4d transition and light rare earth metals, and heavy metals (see Table 1). The additional elements to FIG. 6 are the source 60d, the filter 61d, and the detector 62d.

The timing diagram for the multiple source scanning system is shown in FIGS. 8a through 8f. It is understood that the shown time differences are at arbitrary scale and for illustration purposes only. The lower case letters a, b, c, and d in the x-ray detector 70, analog-to-digital converter 72, and logarithmic operation 74 portions, represent the four energy channels, respectively. The upper case letters A, B, C, and D in the matrix operation 76, image maximization 78, and display 80 portions represent the four material groups, respectively. As the luggage or object moves in, the image data is acquired by the detectors 70 in the order of a-b-c-d due to the source-detector pair positions. The time lag between the detection is previously given by $\Delta T=L/|\bar{v}|$, assuming that the conveyor belt is in a steady motion. After the initial data acquisition 70, the image data are analog-to-digital converted 72 in each of the individual energy channels a, b, c, and d. The onset of 72a has a very small time delay from the onset of 70a due to electronic propagation and can be neglected for the practical time scale considered for real-time imaging. Between the individual energy channels a, b, c, and d, the time lag from the conveyor belt motion is maintained. The image data is later transferred, with small propagation delay, to the logarithmic operation 74 along each energy channel and the time lag $\Delta T= L/|\bar{v}|$ between the energy channel still remains. Following the logarithmic operation, the data in each energy channel is sent for the matrix operation 76. The matrix operation does not take place until data from all the four channels arrive at the matrix operation area; therefore the onset of matrix operation 76A, 76B, 76C, and 76D for each material-specific image can only be as soon as the logarithmic operation in channel 74d is started. After the matrix operation, the material-specific images are preliminarily obtained. These images are respectively sent into the image maximization area along channels 76A, 78B, 76C, and 78D. In these channels, the images go through the image processor as described in 36 of FIG. 2 with the previously-loaded processing algorithm and are then sent to memory buffer and digital-to-analog area as described in 38 and 40 of FIG. 2. This operation will take some time, depending on the complexity of the maximization algorithm, but it can be arranged in such a way that the overall timing requirement for the real-time display is met. The last step is to display the processed images on the monitors as described above with reference to 42 of FIG. 2. This display will be real-time, that is, continuous, to the inspector, except that the onset of the image display has a time lag of the order 3 $\Delta T$ from the first acquisition of data in channel 70a.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An x-ray inspection system for separating material-specific images generated by transmitting x-rays through an ensemble of unknown materials, comprising:

generating means for generating and emitting N different x-ray energy distributions, each energy distribution being labelled by $E_k$ and having an x-ray intensity $I_0(E_k)$, where k ranges from 1 to N, and where N is an integer greater than 1;

a device storing an N by N matrix $\mu^{-1}$, where $\mu^{-1}$ is an inversion of a matrix t*, and where each matrix element $\mu_{jk}$ for the matrix $\mu$ is defined as the linear attenuation coefficient of a certain material group j (of N material groups) at the x-ray energy $E_k$, the N material groups being generated from sorting the ensemble of unknown materials into N possible groups of materials according to the closeness of linear attenuation coefficients or equivalent characteristics of materials at different incident x-ray energy distributions prior to inspection, wherein at least two $\mu^{-1}$ matrices are stored in the device and each $\mu^{-1}$ matrix corresponds to a different set of N material groups;

reshaping means for reshaping the N different x-ray energy distributions emitted from the generating means;

first detecting means for detecting the x-ray intensities $I_0(E_k)$ at each of the reshaped N x-ray energy distributions labelled $E_k$, the detecting occurring before transmission of the reshaped N x-ray energy distributions through the ensemble of unknown materials, the first detecting means outputting a first signal corresponding to the detection by the first detecting means;

second detecting means for detecting a portion of the reshaped N x-ray energy distributions labelled $E_k$ that have passed through the ensemble of unknown materials, the second detecting means outputting a second signal corresponding to the detection by the second detecting means;

first converting means for receiving the first signal from the first detecting means and for converting the first signal into first image information;

second converting means for receiving the second signal from the second detecting means and for converting the second signal into second image information;

logarithmic means for logarithmically processing the first and second image information;

switching means for dynamically switching from one $\mu^{-1}$ matrix for one set of N material groups to another $\mu^{-1}$ for another set of N material groups during the inspection, wherein the switching is for the purpose of finding an appropriate set of N material groups that best represents the actual material groups existing in the ensemble under inspection;

image-generating means for generating material-specific images for the N groups of materials, using the logarithmically processed first and second image information and the $\mu^{-1}$ matrix; and processing means for processing and displaying the material-specific images.

2. The x-ray inspection system according to claim 1, wherein the detecting means comprises a semiconductor detector.

3. The x-ray inspection system according to claim 1, wherein luggage is carried past the inspection system on a conveyer belt.

4. The x-ray inspection system according to claim 1, further comprising N displays, each displaying one of the N material groups.

5. The x-ray inspection system according to claim 1, further comprising controlling means for controlling one or more of the following: the operation and timing of the generating means, the reshaping means, the first and second detecting means, the first and second converting means, the logarithmic means, the switching means, image receivers, the image-generating means, the processing means, and a conveyer belt.

6. The x-ray inspection system according to claim 1, wherein the controlling means includes means for controlling saturation and underexposure.

7. The x-ray inspection system according to claim 1, wherein the controling means includes means for controlling an amount of light entering the first and second detecting means by controlling x-ray intensity.

8. The x-ray inspection system according to claim 1, wherein the inspection operates to display the material-specific images in real-time.

9. An x-ray inspection system for separating material-specific images generated by transmitting x-rays through an ensemble of unknown materials, comprising:

generating means for generating and emitting N different x-ray energy distributions, each energy distribution being labelled by $E_k$ and having an x-ray intensity $I_0(E_k)$, where k ranges from 1 to N, and where N is an integer greater than 1;

a device storing an N by N matrix $\mu^{-1}$, where $\mu^{-1}$ is the inversion of a matrix $\mu$, and where each matrix element $\mu_{jk}$ for the matrix $\mu$ is defined as the linear attenuation coefficient of a certain material group j (of N material groups) at the x-ray energy $E_k$, the N material groups being generated from sorting the ensemble of unknown materials into N possible groups of materials according to closeness of linear attenuation coefficients or equivalent characteristics of materials at different incident x-ray energy distributions prior to inspection;

reshaping means for reshaping the N different x-ray energy distributions emitted from the generating means;

first detecting means for detecting the x-ray intensities $I_0(E_k)$ at each of the reshaped N x-ray energy distributions labelled $E_k$, the detecting occurring before transmission of the reshaped N x-ray energy distributions through the ensemble of unknown materials, the first detecting means outputting a first signal corresponding to the detection by the first detecting means;

second detecting means for detecting a portion of the reshaped N x-ray energy distributions labelled $E_k$ that have passed through the ensemble of unknown materials, the second detecting means outputting a second signal corresponding to the detection by the second detecting means;

first converting means for receiving the first signal from the first detecting means and for converting the first signal into first image information;

second converting means for receiving the second signal from the second detecting means and for convening the second signal into second image information;

logarithmic means for logarithmically processing the first and second image information;

means for generating material-specific images for the N groups of materials, using the logarithmically processed first and second image information and the matrix $\mu^{-1}$; and means for processing and displaying the material-specific images.

10. The x-ray inspection system according to claim 9, wherein luggage is carried past the inspection system on a conveyer belt.

11. The x-ray inspection system according to claim 9, further comprising N displays, each displaying one of the N material groups.

12. The x-ray inspection system according to claim 9, wherein the means for generating material-specific images incorporates a matrix operation using N independent arithmetic channels where each independent channel corresponds to one independent vector component of the vector, and where N is a dimension of the vectors.

13. The x-ray inspection system according to claim 9, wherein the inspection operates to display the material-specific images in real-time.

14. The x-ray inspection system according to claim 9, further comprising controlling means for controlling one or more of the following: the operation and timing of the generating means, the reshaping means, the first and second detecting means, the first and second converting means, the logarithmic means, a switching means, image receivers, the image-generating means, the processing means, and a conveyer belt.

15. The x-ray inspection system according to claim 9, further including controlling means for controlling saturation and underexposure.

16. The x-ray inspection system according to claim 9, further including controling means for controlling an amount of light entering the first and second detecting means by controlling x-ray intensity.

17. An x-ray inspection system for separating material-specific images generated by transmitting x-rays through an ensemble of unknown materials, comprising:

generating means for generating and emitting N different x-ray energy distributions, each energy distribution being labelled by $E_k$ and having an x-ray intensity $I_0(E_k)$, where k ranges from 1 to N, and where N is an integer greater than 1, the generation means comprising at least two different x-ray sources simultaneously emitting two different x-ray energies;

a device storing an N by N matrix $\mu^{-1}$, where $\mu^{-1}$ is the inversion of a matrix $\mu$, and where each matrix element $\mu_{jk}$ for the matrix$\mu$ is defined as the linear attenuation coefficient of a certain material group j (of N material groups) at the x-ray energy $E_k$, the N material groups being generated from sorting the ensemble of unknown materials into N possible groups of materials according to closeness of linear attenuation coefficients or equivalent characteristics of materials at different incident x-ray energy distributions prior to inspection;

reshaping means for reshaping the N different x-ray energy distributions emitted from the generating means;

first detecting means for detecting the x-ray intensities $I_0(E_k)$ at each of the reshaped N x-ray energy distributions labelled $E_k$, the detecting occurring before transmission of the reshaped N x-ray energy distributions through the ensemble of unknown materials, the first detecting means outputting a first signal corresponding to the detection by the first detecting means;

second detecting means comprising at least two detectors functioning simultaneously, for detecting a portion of the reshaped N x-ray energy distributions labelled $E_k$ that have passed through the ensemble of unknown materials, the second detecting means outputting a second signal corresponding to the detection by the second detecting means;

scanning means for performing simultaneous scanning of x-ray energies by moving either the x-ray sources or the ensemble of unknown materials;

correcting means for correcting an image time lag which originates from spatial arrangements of the x-ray sources and detectors, by considering the speed of the ensemble of unknown material or the x-ray sources in motion;

first converting means for receiving the first signal from the first detecting means and for convening the first signal into first image information;

second converting means for receiving the second signal from the second detecting means and for converting the second signal into second image information;

logarithmic means for logarithmically processing the first and second image information;

image-generating means for generating material-specific images for the N groups of materials, using the logarithmically processed first and second image information and the matrix $\mu^{-1}$; and means for processing and displaying the material-specific images.

18. The x-ray inspection system according to claim 17, further comprising controlling means for controlling one or more of the following: the scanning means, the operation and timing of the generating means, the reshaping means, the first and second detecting means, the first and second converting means, the logarithmic means, a switching means, image receivers, the image-generating means, the processing means, and a conveyer belt.

19. The x-ray inspection system according to claim 17, wherein the detecting means comprises a semiconductor detector.

20. The x-ray inspection system according to claim 17, further comprising controlling means for controlling image saturation and underexposure.

21. The x-ray inspection system according to claim 17, wherein the scanning means comprises a conveyer belt.

22. The x-ray inspection system according to claim 17, wherein the scanning means comprises means for moving the generating means past an object containing the ensemble of unknown materials.

23. The x-ray inspection system according to claim 17, further comprising N displays, each displaying one of the N material groups.

24. The x-ray inspection system according to claim 17, wherein the inspection operates to display the material-specific images in real-time.

25. The x-ray inspection system according to claim 17, wherein the controlling means includes means for controlling saturation and underexposure.

26. The x-ray inspection system according to claim 17, wherein the controling means includes means for controlling an amount of light entering the first and second detecting means by controlling x-ray intensity.

27. An x-ray inspection system for separating material-specific images generated by transmitting x-rays through an ensemble of unknown materials, comprising:

generating means for generating and emitting N different x-ray energy distributions, each energy distribution being labelled by $E_k$ and having an x-ray intensity $I_0(E_k)$, where k ranges from 1 to N, and where N is an integer greater than 1;

a device storing an N by N matrix $\mu^{-1}$, where $\mu^{-1}$ is the inversion of a matrix $\mu$, and where each matrix element $\mu_{jk}$ for the matrix $\mu$ is defined as the linear attenuation coefficient of a certain material group j (of N material groups) at the x-ray energy $E_k$, the N material groups being generated from sorting the ensemble of unknown materials into N possible groups of materials according to the closeness of linear attenuation coefficients or equivalent characteristics of materials at different incident x-ray energy distributions prior to inspection;

reshaping means for reshaping the N different x-ray energy distributions emitted from the generating means;

first detecting means for detecting the x-ray intensities $I_0(E_k)$ at each of the reshaped N x-ray energy distributions labelled $E_k$, the detecting occurring before transmission of the reshaped N x-ray energy distributions through the ensemble of unknown materials, the first detecting means outputting a first signal corresponding to the detection by the first detecting means;

second detecting means for detecting a portion of the reshaped N x-ray energy distributions labelled $E_k$ that have passed through the ensemble of unknown materials, the second detecting means outputting a second signal corresponding to the detection by the second detecting means;

first converting means for receiving the first signal from the first detecting means and for converting the first signal into first image information;

second converting means for receiving the second signal from the second detecting means and for converting the second signal into second image information;

splitting means for splitting or transporting the second image information at different x-ray energies among at least two image receivers;

controlling means for controlling the timing of the generating means, the reshaping means, second detecting means, image receivers, and for controlling the timing of acquisition and processing of the second image information at each image receiver;

logarithmic means for logarithmically processing the first and second image information;

means for generating material-specific images for the N groups of materials, using the logarithmically processed first and second image information and the matrix $\mu^{-1}$; and means for processing and displaying the material-specific images.

28. The x-ray inspection system according to claim 27, wherein the detecting means comprises a semiconductor detector.

29. The x-ray inspection system according to claim 27, wherein the splitting means comprises fiber optics.

30. The x-ray inspection system according to claim 27, wherein luggage is carried past the inspection system on a conveyer belt.

31. The x-ray inspection system according to claim 27, wherein the controlling means includes means for controlling saturation and underexposure.

32. The x-ray inspection system according to claim 27, wherein the controling means includes means for controlling an amount of light entering the first and second detecting means by controlling x-ray intensity.

33. The x-ray inspection system according to claim 27, further comprising at least one image processor in addition to the controlling device as set forth in claim 5 where the purpose of the image processors is to improve the display of processed images from previous steps.

34. The x-ray inspection system according to claim 27, further comprising controlling means for controlling one or more of the following: the operation and timing of the generating means, the reshaping means, the first and second detecting means, the first and second converting means, the splitting means, image receivers, the image receivers, the logarithmic means, a switching means, the image-generating means, the processing means, and a conveyer belt.

35. The x-ray inspection system according to claim 27, wherein the inspection operates to display the material-specific images in real-time.

36. An x-ray inspection system for separating material-specific images generated by transmitting x-rays through an ensemble of unknown materials, comprising:

generating means for generating and emitting N different x-ray energy distributions, each energy distribution being labelled by $E_k$ and having an x-ray intensity $I_0(E_k)$, where k ranges from 1 to N, and where N is an integer equal to two;

a device storing an N by N matrix $\mu$, where $\mu^{-1}$ is an inversion of a matrix $\mu$, and where each matrix element $\mu_{jk}$ for the matrix $\mu$ is defined as the linear attenuation coefficient of a certain material group j (of N material groups) at the x-ray energy $E_k$, the N material groups being generated from sorting the ensemble of unknown materials into N possible groups of materials according to the closeness of linear attenuation coefficients or equivalent characteristics of materials at different incident x-ray energy distributions prior to inspection, wherein at least one $\mu^{-1}$ matrice are stored in the device and each $\mu^{-1}$ matrix corresponds to a different set of N material groups;

reshaping means for reshaping the N different x-ray energy distributions emitted from the generating means;

detecting means for detecting a portion of the reshaped N x-ray energy distributions labelled $E_k$ that have passed through the ensemble of unknown materials, the detecting means outputting a signal corresponding to the detection by the detecting means;

converting means for receiving the signal from the detecting means and for converting the signal into image information;

logarithmic means for logarithmically processing the image information;

switching means for dynamically switching from one $\mu^{-1}$ matrix for one set of N material groups to another $\mu^{-1}$ for another set of N material groups during the inspection when more than one $\mu^{-1}$ matrices have been stored, wherein the switching is for the purpose of finding an appropriate set of N material groups that best represents the actual material groups existing in the ensemble under inspection;

image-generating means for generating material-specific images for the N groups of materials, using the logarithmically processed image information and the $\mu^{-1}$ matrix; and processing means for processing and displaying the material-specific images.

37. The x-ray inspection system according to claim 36, wherein luggage is carried past the inspection system on a conveyer belt.

38. The x-ray inspection system according to claim 36, further comprising N displays, each displaying one of the N material groups.

39. The x-ray inspection system according to claim 36, wherein the means for generating material-specific images incorporates a matrix operation using N independent arithmetic channels where each independent channel corresponds to one independent vector component of the vector, and where N is a dimension of the vectors.

40. The x-ray inspection system according to claim 36, wherein the inspection operates to display the material-specific images in real-time.

41. The x-ray inspection system according to claim 36, further comprising controlling means for controlling one or more of the following: the operation and timing of the generating means, the reshaping means, the detecting means, the converting means, the logarithmic means, a switching means, image receivers, the image-generating means, the processing means, and a conveyer belt.

42. The x-ray inspection system according to claim 36, further including controlling means for controlling saturation and underexposure.

43. The x-ray inspection system according to claim 36, further including controling means for controlling an amount of light entering the detecting means by controlling x-ray intensity.

* * * * *